United States Patent [19]

Suzuki et al.

[11] Patent Number: 5,202,054
[45] Date of Patent: Apr. 13, 1993

[54] LIQUID CRYSTAL COMPOUND

[75] Inventors: Yoshiichi Suzuki; Hiroyuki Mogamiya; Noriko Yamakawa, all of Tokyo, Japan

[73] Assignee: Showa Shell Sekiyu K.K., Tokyo, Japan

[21] Appl. No.: 646,898

[22] Filed: Jan. 28, 1991

[30] Foreign Application Priority Data

Jan. 26, 1990 [JP] Japan .................................. 2-17458

[51] Int. Cl.$^5$ ..................... C09K 19/34; C07D 239/02
[52] U.S. Cl. ........................... 252/99.61; 252/299.67; 544/242; 544/335
[58] Field of Search ........................ 252/299.01, 299.61, 252/299.62, 299.65, 299.66; 544/242, 246, 335

[56] References Cited

U.S. PATENT DOCUMENTS 4,764,636  8/1988  Sasaki et al. ..................... 544/296
4,918,213  4/1990  Nohira et al. ................... 252/299.61
4,921,632  4/1990  Nakamura et al. ............ 252/299.61

FOREIGN PATENT DOCUMENTS 0224725  6/1987  European Pat. Off. .
0301511  2/1989  European Pat. Off. .
1-139551  6/1989  Japan .
2-255661  10/1990  Japan .

OTHER PUBLICATIONS

Derwent Abstract of JP-A-2-255661.

Primary Examiner—Robert L. Stoll
Assistant Examiner—Shean C. Wu
Attorney, Agent, or Firm—Sughrue, Mion, Zinn, Macpeak & Seas

[57] ABSTRACT

A liquid crystal compound represented by formula (I):

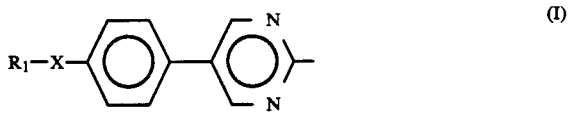

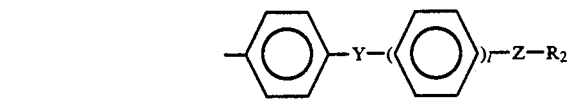

wherein $R_1$ represents an alkyl group having from 1 to 18 carbon atoms; $R_2$ represents an optically active group represented by formula (II), (III) or (IV):

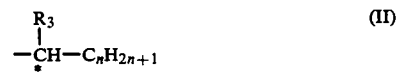

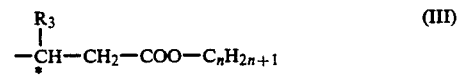

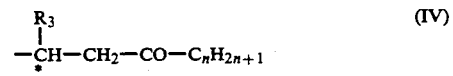

wherein $R_3$ represents a lower halo-alkyl group having from 1 to 2 carbon atoms; X represents —O—, —COO—, —OCO— or a single bond; Y represents —CH$_2$O— or —COO—; and Z represents —COO— or —O—, l represents 0 or 1, provided that when l is 0, Y is a single bond; n represents an integer of from 1 to 18; and * indicates an optically active center. The compound exhibits three stable states of molecular orientation.

3 Claims, 3 Drawing Sheets

ELECTRO-OPTIC RESPONSE OF TRISTABLE LIQUID CRYSTAL OF INVENTION

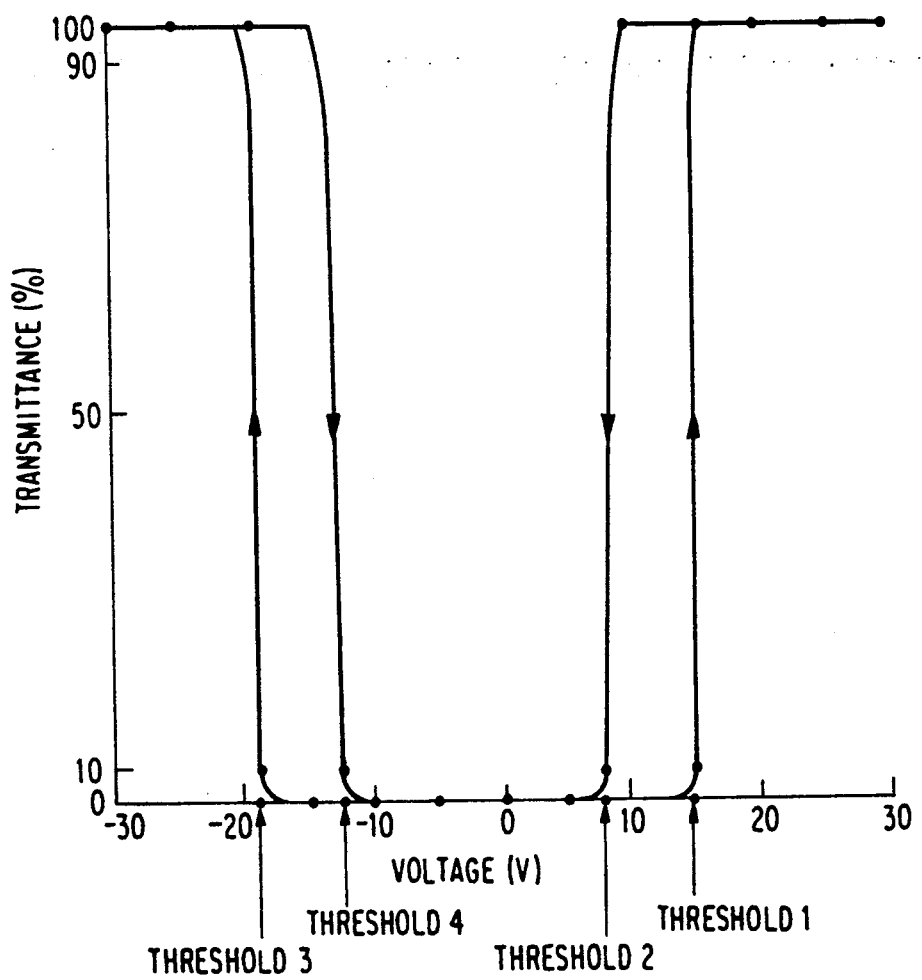

TRIANGULAR WAVE VOLTAGE APPLIED

ELECTRO-OPTIC RESPONSE OF COMMERCIAL NEMATIC LIQUID CRYSTAL

ELECTRO-OPTIC RESPONSE OF CONVENTIONAL BISTABLE LIQUID CRYSTAL

ELECTRO-OPTIC RESPONSE OF TRISTABLE LIQUID CRYSTAL OF INVENTION

LIQUID CRYSTAL COMPOUND

FIELD OF THE INVENTION

This invention relates to a ferroelectric liquid crystal compound which is suitable for use in display elements or electro-optic elements utilizing response to an electric field.

This invention also relates to a ferroelectric liquid crystal compound exhibiting three stable states of molecular orientation (hereinafter referred to as tristable states or, simply, three states) which is suitable for use in display elements, electro-optic elements, non-linear optical elements, etc. utilizing response to an electric field.

BACKGROUND OF THE INVENTION

Liquid crystal elements have been put into practical use in various applications, such as watches, table calculators, personal computers, and miniaturized liquid crystal TV on account of their electro-optic effects. Most of the liquid crystal display elements now in practical use utilize dielectric alignment effect of nematic liquid crystals or cholesteric liquid crystals. However, these liquid crystals have insufficient multiplex driving characteristics to cope with an increase in display capacity and are therefore limited in possibility of broadening of a display area. Moreover, they have a very slow electro-optic response and require a switching time from several tens milliseconds to several hundreds milliseconds. These problems have been a technical bar to development of liquid crystal displays with large capacity, large area, and high rate of response. It has thus been keenly demanded to develop a novel liquid crystal material by which these technical problems can be overcome.

Ever since it was reported that ferroelectric liquid crystals prepared from optically active compounds can be driven at a high speed on the order of microsecond and maintain their stable molecular states to exert a memory effect, a number of ferroelectric liquid crystals including Schiff base compounds, biphenyl compounds, benzoic ester compounds, and pyrimidine compounds have been synthesized, studied, and partly put into practical use to date. However, Schiff base compounds have difficulties on practical use due to the unsaturated double bond thereof and lability to water. Use of pyrimidine compounds as liquid crystal has been proposed in JP-A-57-95965 and JP-A-61-129169 (the term "JP-A" as used herein means an "unexamined published Japanese patent application"), but the proposed pyrimidine compounds do not have a sufficiently broad range of phase transition temperature inclusive of room temperature. Up to date, there has been developed no liquid crystal material which, even when used alone, exhibits a liquid crystal phase in a broad temperature range from low to high, has a low viscosity coefficient and is expected to have a high response rate, has a proper birefringence for obtaining a high display contrast, and exhibits a series of phases for realizing satisfactory orientation characteristics. That is, currently available liquid crystal materials are multi-component mixed liquid crystal compositions comprising several different kinds of liquid crystal compounds. Thus, from the aspect of liquid crystal materials, development of a novel liquid crystal having high performance properties has been demanded.

On the other hand, various electro-optic devices using ferroelectric liquid crystals have hitherto been developed. For example, several high speed electro-optic devices using ferroelectric liquid crystals have been proposed to date. Typically, such devices include an element in which a twisted structure is untwisted by the force of wall surfaces, and two direction of molecular orientation in parallel in the wall surfaces are varied by changing the polarity of an applied electric field as described, e.g., in JP-A-56-107216.

The use of a compound showing ideal two states (bistable compound) having an electric field response waveform as shown in FIG. 1 is prerequisite in the above-described devices. However, such a compound exhibiting ideal two states is not yet available. The so far synthesized bistable liquid crystals have a response waveform as shown in FIG. 2, not as shown in FIG. 1. When the state-of-the-art liquid crystals having a response waveform as shown in FIG. 2 are used, for example, in light switching circuits, since transmission gradually changes as the applied voltage changes from negative to positive, the desired results cannot be sufficiently achieved simply by changing the applied voltage between "on" and "off". Moreover, currently available bistable liquid crystals have difficulty in reaching a mono-domain state in their Sc* phase without an applied voltage, i.e., in reaching an ideal molecular orientation state, and easily undergo defect or a molecular orientation disturbance called twist. Thus, it has been difficult to achieve the above-stated ideal two states of molecular orientation over a wide area.

Further, because the threshold value (voltage at which luminance changes by a prescribed value) is low, dynamic driving is liable to suffer from a reduction in contrast or a reduction in the viewing angle.

Furthermore, these conventional bistable liquid crystals do not exhibit a hysteresis loop as shown in FIG. 1, but exhibit hysteresis as shown in FIG. 2 so that they have no memory effect. Therefore, it is necessary to continue applying a voltage of $v_3$ as shown in FIG. 2 or continue applying a high frequency for the liquid crystal to maintain a stable response in the S*c phase, which, in either case, results in a considerable energy consumption.

Thus, conventional electro-optic devices have many defects which need to be overcome, notwithstanding the strong demand for devices which make effective use of the characteristics of electro-optic devices to use an applied electric field to achieve molecular orientation of ferroelectric liquid crystals.

SUMMARY OF THE INVENTION

An object of this invention is to provide not only a novel liquid crystal compound which exhibits two states, but also a novel liquid crystal compound which exhibits stable three molecular orientation (tristable) states having a high light/shade contrast in the absence of an electric field, which has well defined threshold characteristics and a well defined hysteresis curve or loop as shown in FIG. 3, which easily undergoes dynamic driving, and which can be used in liquid crystal electro-optic devices utilizing three states, which make it possible to obtain a high-speed response.

More specifically, an object of this invention is to provide a novel ferroelectric liquid crystal having a phenylpyrimidine skeleton which exhibits excellent properties for practical use, such as chemical stability and compatibility.

Another object of this invention is to provide a novel ferroelectric liquid crystal showing antiferroelectric properties which exhibits three stable states of molecular orientation which are entirely different from a chiral smectic C phase (Sc* phase) which is a conventional bistable state phase.

The terminology "three states" as used herein means three stable molecular orientation states as now explained. In a liquid crystal electro-optic device comprising a pair of electrode substrates with a prescribed gap therebetween and a ferroelectric liquid crystal sandwiched between the pair of substrates, the electrodes being connected to an electric power source so that voltage of triangular wave as shown in FIG. 4(A) can be applied thereto, the ferroelectric liquid crystal shows a first stable molecular orientation state as shown by numeral 2 of FIG. 4(D) when no electric field is applied thereto, a second stable molecular orientation state as shown by numeral 1 of FIG. 4(D) differing from the first stable state when an electric field is applied to one direction, and a third stable molecular orientation state as shown by numeral 3 of FIG. 4(D) differing from either of the first and second stable states when an electric field is applied to another direction. With respect to liquid crystal electro-optic devices utilizing these three stable states, the inventors have already filed in JP-A-2-153322.

On the contrary, "commercially available nematic liquid crystals" and so far synthesized bistable liquid crystals do not have such three stable states, as shown in FIGS. 4(B) and (C), respectively.

The above-described tristable ferroelectric liquid crystals according to the present invention produce striking effects when applied to liquid crystal displays as compared with conventional nematic liquid crystals as now discussed.

While conventional liquid crystals must be driven using a very complicated system called an active matrix system, the tristable ferroelectric liquid crystals of the present invention can be driven using a simple matrix display system. Accordingly, a display element using the tristable ferroelectric liquid crystal can be produced in a simple manner, which makes it feasible to widen the display area and to reduce production costs, whereas conventional display elements require complicated production steps, encounter difficulty in widening the display area, and involve high production costs.

The present invention provides a liquid crystal compound comprising a pyrimidine derivative represented by formula (I):

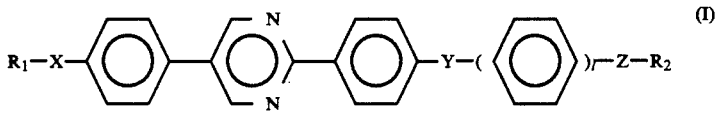

wherein $R_1$ represents an alkyl group having from 1 to 18, preferably 6 to 12, carbon atoms; $R_2$ represents an optically active group represented by formula (II), (III) or (IV):

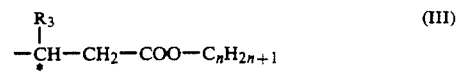

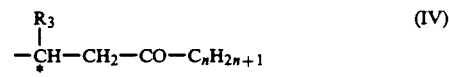

wherein $R_3$ represents a lower halo-alkyl group having from 1 to 2 carbon atoms; X represents —O—, —COO—, —OCO— a single bond; Y represents —CH$_2$O— or —COO—; and Z represents —COO— or —O—, l represents 0 or 1, provided that when l is 0, Y is a single bond; n represents an integer of from 1 to 18; and * indicates an optically active center.

BRIEF DESCRIPTION OF THE DRAWING

FIGS. 1, 2, and 3 each show the hysteresis curve or loop of an ideal bistable liquid crystal (which is not actually available), of a conventionally synthesized bistable liquid crystal, and of a tristable liquid crystal according to the present invention, respectively, in which the applied voltage is plotted as the abscissa and the transmittance (%) as the ordinate.

DETAILED DESCRIPTION OF THE INVENTION

Figure 1:
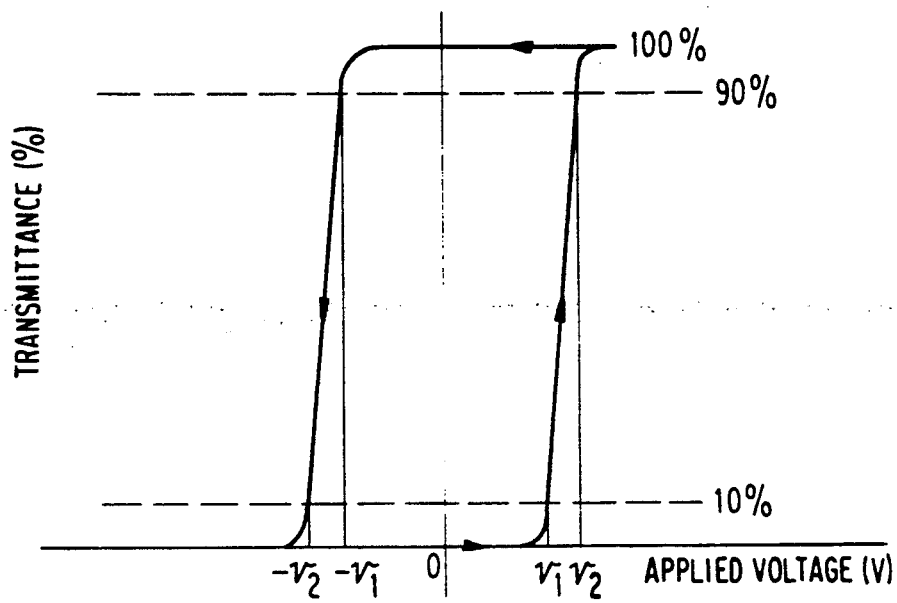
Figure 2:
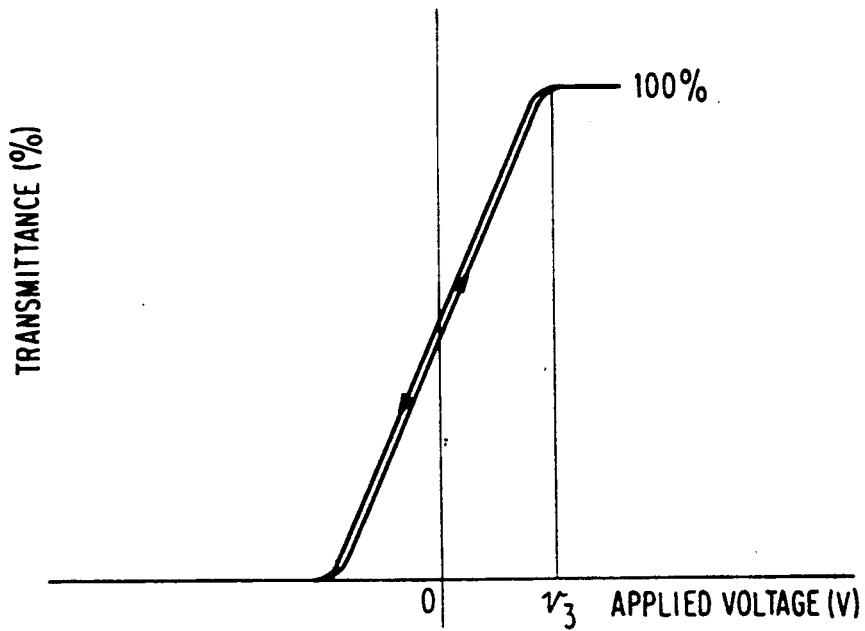
Figure 4A:
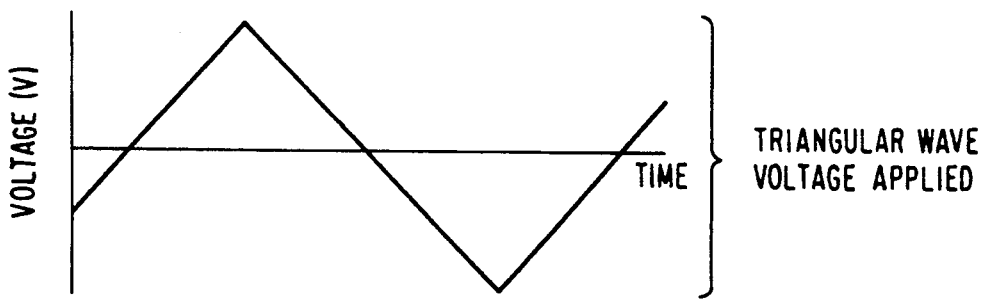
FIG. 4(A) shows the triangular wave voltage applied.
Figure 4B:
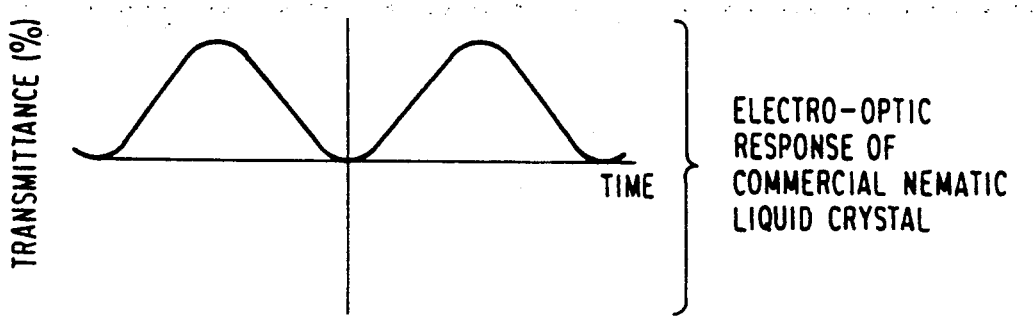
FIGS. 4(B), (C), and (D) each show the electro-optic response of a commercially available nematic liquid crystal, a conventionally synthesized bistable liquid crystal, and a tristable liquid crystal according to the present invention, respectively, when the triangular wave of FIG. 4(A) is applied.
Figure 4C:
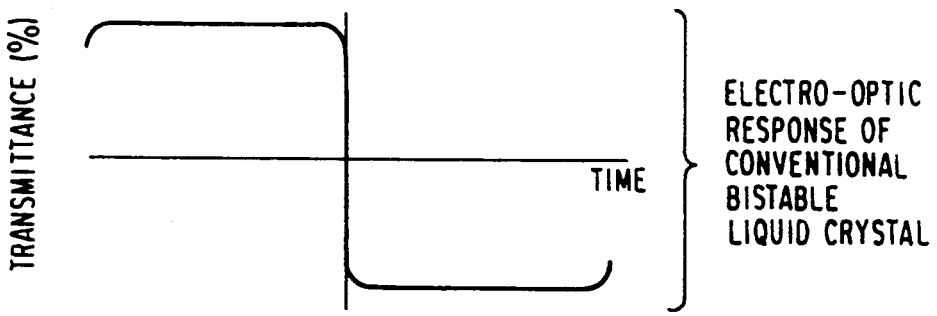
Figure 4D:
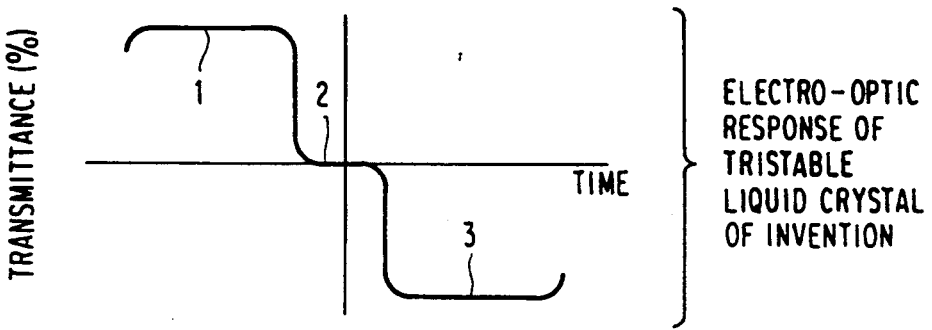

In formula (I), specific examples of the lower halo-alkyl group as represented by $R_3$ include $CF_3$, $C_2F_5$, $CHF_2$, $CH_2F$, $CFClH$, $CCl_3$, $CClF_2$, and $C_2Cl_2F_3$. $R_3$ preferably represents $C_2F_3$, and more preferably $C_2F_5$.

Of the pyrimidine derivatives represented by formula (I), those represented by formula (V):

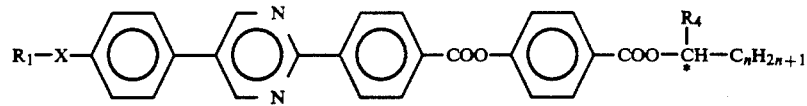

wherein $R_1$, X, n, and * have the same meanings as defined above; and $R_4$ represents $CF_3$ or $C_2F_5$, are particularly preferred because of their excellent three stable states.

The liquid crystal compounds according to the present invention can be synthesized according to the following processes (A), (B) or (C).

Process (A)

A 4-[5-(4-alkoxyphenyl)-2-pyrimidinyl]phenyl-4′-carboxylic acid chloride represented by formula (IX):

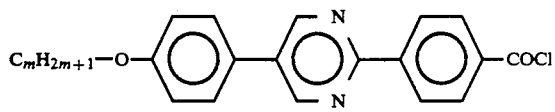

wherein m represents an integer of from 1 to 18, is reacted directly with an optically active halogen-containing alcohol, e.g., (R)-(+)- or (S)-(−)-1,1,1-trifluoro-2-alkanol, etc.

Process (B)

4-Benzyloxybenzoic acid is converted to its acid chloride with a chlorinating reagent, e.g., thionyl chloride, which is then reacted with an (R)-(+)- or (S)-(−)-trifluoro-2-alkanol to obtain an ester. The ester is subjected to debenzylation, and the resulting phenol compound (X) is reacted with a 4-[5-(4-alkyloxyphenyl)-2-pyrimidinyl]phenyl-4′-carboxylic acid chloride (IX) to obtain a desired compound (XI).

The 4-[5-(4-alkoxyphenyl)-2-pyrimidinyl]phenyl-4′-carboxylic acid chloride (IX) which can be used as a starting material in processes (A) and (B) can be synthesized according to the following reaction scheme:

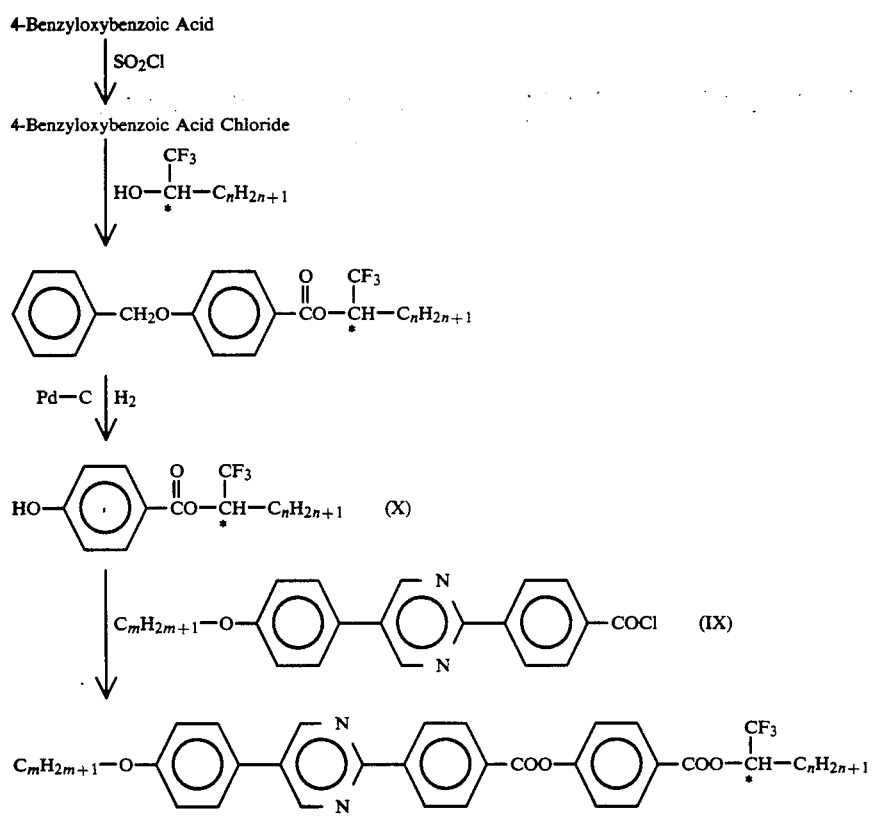

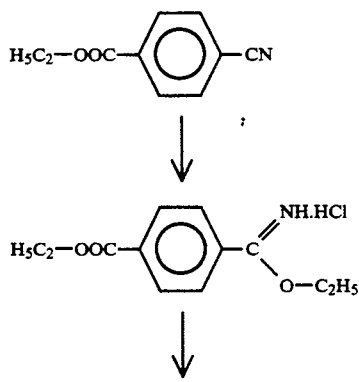

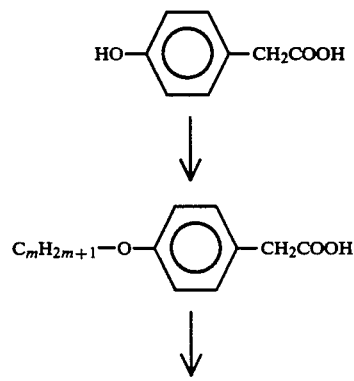

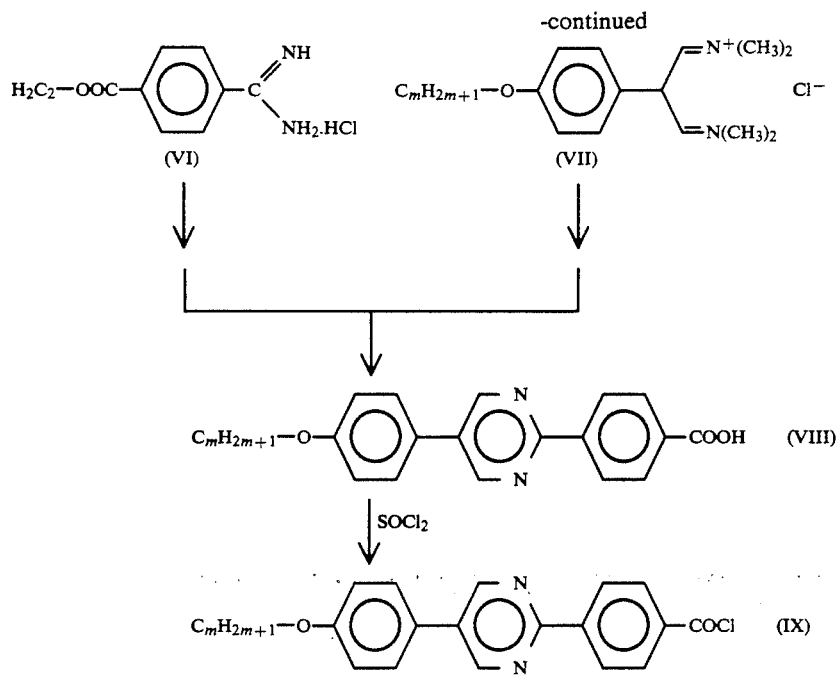

Process (C)

A 4-[5-(4-alkoxyphenyl)-2-pyrimidinyl]phenyl-4'-carboxylic acid (VIII) shown above and a phenol derivative of (R)-(+)- or (S)-(−)-1,1,1-trifluoro-2-alkanol (X) shown above are subjected to dehydrating condensation in the presence of a condensating agent, e.g., dicyclohexylcarbodiimide.

The 4-[5-(4-alkoxyphenyl)-2-pyrimidinyl]phenyl-4'-carboxylic acid (VIII) can be prepared by the process disclosed in JP-A-60-260564, in which an intermediate (VII) derived from a substituted phenylacetic acid and a benzamidine hydrochloride (VI) are reacted under a basic condition, as illustrated by the above reaction scheme.

Optically active halogen-containing alcohols which can be preferably used in the above-described processes include those corresponding to formula (II), e.g., 1,1,1-trifluoro-2-hexanol, 1,1,1-trifluoro-2-heptanol, 1,1,1-trifluoro-2-octanol, 1,1,1-trifluoro-2-nonal, 1,1,1-trifluoro-2-decanol, 1,1,1-trifluoro-2-undecanol, 1,1,1-trifluoro-2-dodecanol, 1,1,1-trifluoro-2-tridecanol, 1,1,1-trifluoro-2-tetradecanol, 1,1,1-trifluoro-2-pentadecanol, 1,1,1-trifluoro-2-hexadecanol, 1,1,1-trifluoro-2-heptadecanol, and 1,1,1-trifluoro-2-octadecanol; those corresponding to formula (III), e.g., propyl 1,1,1-trifluoro-2-hydroxybutanoate, butyl 1,1,1-trifluoro-2-hydroxybutanoate, pentyl 1,1,1-trifluoro-2-hydroxybutanoate, hexyl 1,1,1-trifluoro-2-hydroxybutanoate, heptyl 1,1,1-trifluoro-2-hydroxybutanoate, octyl 1,1,1-trifluoro-2-hydroxybutanoate, nonyl 1,1,1-trifluoro-2-hydroxybutanoate, decyl 1,1,1-trifluoro-2-hydroxybutanoate, undecyl 1,1,1-trifluoro-2-hydroxybutanoate, dodecyl 1,1,1-trifluoro-2-hydroxybutanoate, tridecyl 1,1,1-trifluoro-2-hydroxybutanoate, tetradecyl 1,1,1-trifluoro-2-hydroxybutanoate, pentadecyl 1,1,1-trifluoro-2-hydroxybutanoate, and hexadecyl 1,1,1-trifluoro-2-hydroxybutanoate; and those corresponding to formula (IV), e.g., 1,1,1-trifluoro-2-hydroxypropyl propyl ketone, 1,1,1-trifluoro-2-hydroxypropyl butyl ketone, 1,1,1-trifluoro-2-hydroxypropyl pentyl ketone, 1,1,1-trifluoro-2-hydroxypropyl hexyl ketone, 1,1,1-trifluoro-2-hydroxypropyl heptyl ketone, 1,1,1-trifluoro-2-hydroxypropyl octyl ketone, 1,1,1-trifluoro-2-hydroxypropyl nonyl ketone, 1,1,1-trifluoro-2-hydroxypropyl decyl ketone, 1,1,1-trifluoro-2-hydroxypropyl undecyl ketone, 1,1,1-trifluoro-2-hydroxypropyl dodecyl ketone, 1,1,1-trifluoro-2-hydroxypropyl tridecyl ketone, 1,1,1-trifluoro-2-hydroxypropyl tetradecyl ketone, 1,1,1-trifluoro-2-hydroxypropyl pentadecyl ketone, 1,1,1-trifluoro-2-hydroxypropyl hexadecyl ketone, 1,1,1-trifluoro-2-hydroxypropyl heptadecyl ketone, and 1,1,1-trifluoro-2-hydroxypropyl octadecyl ketone.

Illustrative examples of the liquid crystal compounds according to the present invention are shown below.

1) 2-[4-(1,1,1-Trifluoro-2-decyloxycarbonyl)phenyl]-5-(4-hexyloxyphenyl)pyrimidine
2) 2-[4-(1,1,1-Trifluoro-2-decyloxycarbonyl)phenyl]-5-(4-heptyloxyphenyl)pyrimidine
3) 2-[4-(1,1,1-Trifluoro-2-decyloxycarbonyl)phenyl]-5-(4-octyloxyphenyl)pyrimidine
4) 2-[4-(1,1,1-Trifluoro-2-decyloxycarbonyl)phenyl]-5-(4-nonyloxyphenyl)pyrimidine
5) 2-[4-(1,1,1-Trifluoro-2-decyloxycarbonyl)phenyl]-5-(4-decyloxyphenyl)pyrimidine
6) 2-[4-(1,1,1-Trifluoro-2-decyloxycarbonyl)phenyl]-5-(4-undecyloxyphenyl)pyrimidine
7) 2-[4-(1,1,1-Trifluoro-2-decyloxycarbonyl)phenyl]-5-(4-dodecyloxyphenyl)pyrimidine
8) 2-[4-(3-Propyloxycarbonyl-1,1,1,-trifluoro-2-propyloxycarbonyl)phenyl]-5-(4-octyloxyphenyl)-pyrimidine
9) 2-[4-(3-Butyloxycarbonyl-1,1,1-trifluoro-2-propyloxycarbonyl)phenyl]-5-(4-octyloxyphenyl)pyrimidine
10) 2-[4-(3-Pentyloxycarbonyl-1,1,1-trifluoro-2-propyloxycarbonyl)phenyl]-5-(4-octyloxyphenyl)-pyrimidine
11) 2-[4-(1-Hexyloxycarbonyl-1,1,1-trifluoro-2-propyloxycarbonyl)phenyl]-5-(4-octyloxyphenyl)-pyrimidine 12) 2-[4-(3-Heptyloxycarbonyl-1,1,1-trifluoro-2-propyloxycarbonyl)phenyl]-5-(4-octyloxyphenyl)-pyrimidine
13) 2-[4-(3-Octyloxycarbonyl-1,1,1-trifluoro-2-propyloxycarbonyl)phenyl]-5-(4-octyloxyphenyl)-pyrimidine
14) 2-[4-(3-Nonyloxycarbonyl-1,1,1-trifluoro-2-propyloxycarbonyl)phenyl]-5-(4-octyloxyphenyl)-pyrimidine
15) 2-[4-(3-Decyloxycarbonyl-1,1,1-trifluoro-2-propyloxycarbonyl)phenyl]-5-(4-octyloxyphenyl)-pyrimidine
16) 2-[4-(3-Undecyloxycarbonyl-1,1,1-trifluoro-2-propyloxycarbonyl)phenyl]-5-(4-octyloxyphenyl)-pyrimidine
17) 2-[4-(3-Dodecyloxycarbonyl-1,1,1-trifluoro-2-propyloxycarbonyl)phenyl]-5-(4-octyloxyphenyl)-pyrimidine
18) 2-[4-(3-Butanoyl-1,1,1-trifluoro-2-propyloxycarbonyl)phenyl]-5-(4-octyloxyphenyl)pyrimidine
19) 2-[4-(3-Pentanoyl-1,1,1-trifluoro-2-propyloxycarbonyl)phenyl]-5-(4-octyloxyphenyl)pyrimidine
20) 2-[4-(3-Heptanoyl-1,1,1-trifluoro-2-propyloxycarbonyl)phenyl]-5-(4-octyloxyphenyl)pyrimidine
21) 2-[4-(3-Hexanoyl-1,1,1-trifluoro-2-propyloxycarbonyl)phenyl]-5-(4-octyloxyphenyl)pyrimidine
22) 2-[4-(3-Heptanoyl-1,1,1-trifluoro-2-propyloxycarbonyl)phenyl]-5-(4-octyloxyphenyl)pyrimidine
23) 2-[4-(3-Octanoyl-1,1,1-trifluoro-2-propyloxycarbonyl)phenyl]-5-(4-octyloxyphenyl)pyrimidine
24) 2-[4-(3-Nonanoyl-1,1,1-trifluoro-2-propyloxycarbonyl)phenyl]-5-(4-octyloxyphenyl)pyrimidine
25) 2-[4-(3-Decanoyl-1,1,1-trifluoro-2-propyloxycarbonyl)phenyl]-5-(4-octyloxyphenyl)pyrimidine
26) 2-[4-(3-Undecanoyl-1,1,1-trifluoro-2-propyloxycarbonyl)phenyl]-5-(4-octyloxyphenyl)pyrimidine
27) 2-[4-(3-Dodecanoyl-1,1,1-trifluoro-2-propyloxycarbonyl)phenyl]-5-(4-octyloxyphenyl)pyrimidine
28) 4-[5-(4-Pentyloxyphenyl)-2-pyrimidinyl]phenyl 4-(1,1,1,-trifluoro-2-octyloxycarbonyl)phenyl ester
29) 4-[5-(4-Hexyloxyphenyl)-2-pyrimidinyl]phenyl 4-(1,1,1-trifluoro-2-octyloxycarbonyl)phenyl ester
30) 4-[5-(4-Heptyloxyphenyl)-2-pyrimidinyl]phenyl 4-(1,1,1-trifluoro-2-octyloxycarbonyl)phenyl ester
31) 4-[5-(4-Octyloxyphenyl-2-pyrimidinyl]phenyl 4-(1,1,1-trifluoro-2-octyloxycarbonyl)phenyl ester
32) 4-[5-(4-Nonyloxyphenyl)-2-pyrimidinyl]phenyl 4-(1,1,1-trifluoro-2-octyloxycarbonyl)phenyl ester
33) 4-[5-(4-Decyloxyphenyl)-2-pyrimidinyl]phenyl 4-(1,1,1-trifluoro-2-octyloxycarbonyl)phenyl ester
34) 4-[5-(4-Undecyloxyphenyl)-2-pyrimidinyl]phenyl 4-(1,1,1-trifluoro-2-octyloxycarbonyl)phenyl ester
35) 4-[5-(4-Dodecyloxyphenyl)-2-pyrimidinyl]phenyl 4-(1,1,1-trifluoro-2-octyloxycarbonyl)phenyl ester The present invention is now illustrated in greater detail by way of Examples, but it should be understood that the present invention is not deemed to be limited thereto. All the percents and parts are by weight unless otherwise specified.

EXAMPLE 1

Synthesis of 2-[4-(1,1,1-Trifluoro-2-octyloxycarbonyl)phenyl]-5-(4-octyloxyphenyl)pyrimidine

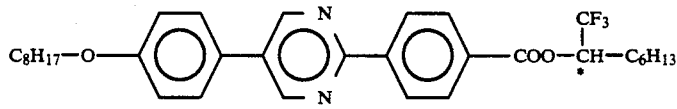

In 20 ml of toluene were added 1.0 g of 4-[5-(4-octyloxyphenyl)pyrimidinyl]phenyl-4'-carboxylic acid and 0.4 g of thionyl chloride, and the mixture was gently refluxed with stirring for 5 hours. The unreacted thionyl chloride and toluene were removed by distillation under reduced pressure to obtain 4-[5-(4-dodecyloxyphenyl)-2-pyrimidinyl]phenyl-4'-carboxylic acid chloride.

A solution of the resulting acid chloride in 10 ml of methylene chloride was added dropwise to a solution of 0.43 g of optically active (R)-(+)-1,1,1-trifluoro-2-octanol ([α]$_D^{20}$= +25.2°), 0.25 g of triethylamine, and a catalytic amount of dimethylaminopyridine in 10 ml of dehydrated methylene chloride at room temperature, followed by stirring for 12 hours. The reaction mixture was poured into ice-water and extracted with methylene chloride. The methylene chloride phase was washed successively with diluted hydrochloric acid, water, an aqueous 1N sodium carbonate solution, and water and dried over anhydrous magnesium sulfate. The solvent was removed by distillation under reduced pressure, and the residual crude product was purified by silica gel column chromatography to obtain 0.81 g of the titled compound ([α]$_D^{20}$= +51.8°).

IR Spectrum (cm$^{-1}$): 1729, 1607, 1437, 1263, 830, 760

The phase transition behavior of the liquid crystal compound obtained was observed under a polarizing microscope using a temperature controlled hot stage in which a liquid crystal cell was placed (hereinafter the same). As a result, the compound exhibited an isotropic phase until the temperature was decreased to 90° C.

EXAMPLE 2

Synthesis of 2-[4-(1,1,1-Trifluoro-2-decyloxycarbonyl)phenyl]-5-(4-octyloxyphenyl)pyrimidine

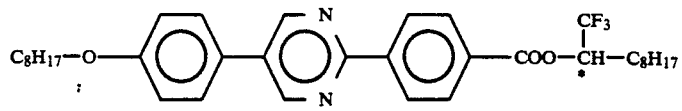

The same procedures as in Example 1 were repeated, except for replacing the optically active (R)-(+)-1,1,1-trifluoro-2-octanol with (R)-(+)-1,1,1-trifluoro-2-decanol, to obtain the titled compound ([α]$_D^{20}$= +52.6°).

IR Spectrum (cm$^{-1}$): 1730, 1607, 1437, 1263, 835, 765

The resulting compound exhibited an isotropic phase until the temperature was decreased to 95° C.

EXAMPLE 3

Synthesis of 2-[4-(3-Hexyloxycarbonyl-1,1,1-trifluoro-2-propyloxycarbonyl)phenyl]-5-(4-octyloxyphenyl)pyrimidine

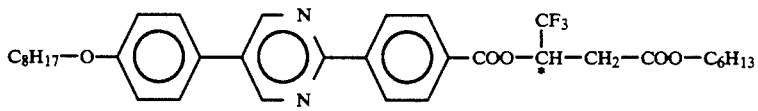

The same procedures as in Example 1 were repeated, except for replacing the optically active (R)-(+)-1,1,1-trifluoro-2-octanol with hexyl (R)-(+)-1,1,1-trifluoro-2-hydroxybutanoate, to obtain the titled compound ($[\alpha]_D^{20} = +27.4°$).

IR Spectrum (cm$^{-1}$): 1741, 1607, 1430, 1263, 831, 757

The resulting compound exhibited the following phase transition.

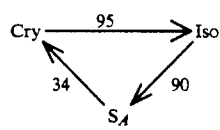

EXAMPLE 4

Synthesis of 4-[5-(4-Octyloxyphenyl)-2-pyrimidinyl]phenyl 4-(1,1,1-Trifluoro-2-octyloxycarbonyl)phenyl Ester In 20 ml of methylene chloride was dissolved 1.1 g of 4-benzyloxybenzoic acid chloride, and to the solution was slowly added a solution of 0.74 g of (R)-(+)-1,1,1-trifluoro-2-octanol ($[\alpha]_D^{20} = +25.2°$), 0 4 g of triethylamine, and a catalytic amount of dimethylaminopyridine in 10 ml of methylene chloride under ice-cooling. After warming to room temperature, the solution was stirred for 12 hours. The reaction mixture was poured into ice-water and extracted with methylene chloride. The methylene chloride phase was successively washed with diluted hydrochloric acid, water, an aqueous 1N sodium carbonate solution, and water and then dried over anhydrous magnesium sulfate. The solvent was removed by distillation under reduced pressure, and the residual crude product was purified by silica gel column chromatography to obtain 1.0 g of 1,1,1-trifluoro-2-octyl 4-benzyloxybenzoate.

The resulting product and 0.1 g of 10% palladium-on-carbon were added to ethanol to conduct debenzylation in a hydrogen atmosphere to obtain 0.76 g of 1-trifluoro-2-octyl 4-hydroxybenzoate.

To 10 ml of methylene chloride were added 0.76 g of the above obtained ester and 0.27 g of triethylamine, and a solution of 1.1 g of 4-[5-(4-dodecyloxyphenyl)-pyrimidyl]phenyl-4'-carboxylic acid chloride in 10 ml of methylene chloride was slowly added thereto at room temperature. The mixture was stirred for a whole day, and the reaction mixture was poured into water and extracted with methylene chloride. The methylene chloride phase was successively washed with diluted hydrochloric acid, water, an aqueous 1N sodium carbonate solution, and water and then dried over anhydrous magnesium sulfate. The solvent was removed by distillation under reduced pressure, and the residual crude product was purified by silica gel column chromatography to obtain 0.97 g of the titled compound ($[\alpha]_D^{20} = +30.9°$).

IR Spectrum (cm$^{-1}$): 1742, 1609, 1437, 1263, 830, 758

The resulting compound exhibited liquid crystal properties and was observed to have the following phase transition temperatures.

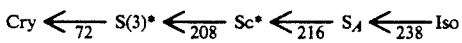

EXAMPLE 5

Ten parts of the liquid crystal compound obtained in Example 1 and 90 parts of a liquid crystal compound

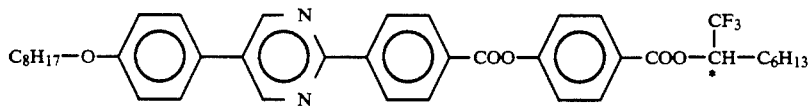

having a smectic C phase shown in Table 1 below were mixed to prepare a liquid crystal composition. The composition was filled into a liquid crystal cell composed of a pair of glass substrates each having an ITO (indium tin oxide) electrode on which a polyimide orientation film had been coated and subjected to a rubbing treatment (cell thickness: 2.6 μm), the glass substrates being assembled in such a manner that the rubbing directions were in parallel.

The resulting cell was slowly cooled at a cooling rate of 0.1 to 1.0° C./min on a temperature controlled hot stage, and the phase transition behavior was observed under a polarizing microscope equipped with a photomultiplier. As a result, it was revealed that the liquid crystal molecules were orientated in an smectic A phase as shown in Table 1 and, further, a mono-domain state could be reached in the chiral smectic C phase thereof. A voltage of ±30 V was applied to the cell to investigate optical response. An electro-clinic effect was observed in a smectic A phase, and optical response of extremely high speed of 28 μsec (Tc−T=30° C.) and a satisfactory contrast were obtained in a chiral smectic C phase.

TABLE 1

| Liquid Crystal Composition | | | Rate of Response (μsec) |
|---|---|---|---|
| Component | Amount (wt %) | Phase Transition Temperature (°C.) | |
|  $Cry \xleftarrow{71} Sc \xleftarrow{162} S_A \xleftarrow{178} N^* \xleftarrow{180} Iso$ | 90 | | |
| Compound of Example 1 | 10 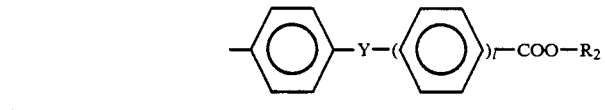 | $Cry \xleftarrow{63} Sc^* \xleftarrow{129} S_A \xleftarrow{177} Iso$ | 28 (Tc − T = 30° C.) |

The similar effects were observed in liquid crystal cells using other compounds obtained in the foregoing examples. The compounds according to the present invention were thus proved useful as a liquid crystal material of a multi-component mixed liquid crystal composition.

As described above, the novel pyrimidine derivatives of the present invention are excellent in chemical stability against heat, light, water, and the like and are therefore practically useful as liquid crystal materials.

Of the pyrimidine derivatives of the present invention, those exhibiting a ferroelectric liquid crystal phase can be used as a single liquid crystal compound in liquid crystal elements and the like. Those having low liquid crystal properties are also useful as a component constituting a liquid crystal composition in combination with other liquid crystal compounds.

The pyrimidine derivatives of the invention shows an S(3)* phase to exhibit three stable states of molecular orientation. On account of such tristability, they find broad applications in electro-optic devices, display devices, switching elements, etc.

Further, the liquid crystal compounds of the present invention have an electro-clinic effect in their smectic A phase with an applied voltage and are thus applicable to various types of light shutters and light printer heads.

While the invention has been described in detail and with reference to specific embodiments thereof, it will be apparent to one skilled in the art that various changes and modifications can be made therein without departing from the spirit and scope thereof.

What is claimed is:

1. A liquid crystal compound represented by formula (I):

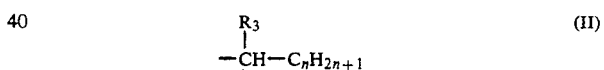
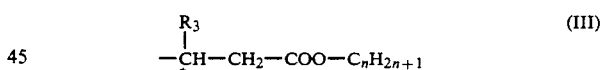

wherein $R_1$ represents an alkyl group having from 1 to 18 carbon atoms; $R_2$ represents an optically active group represented by formula (II), (III) or (IV):

$$-\underset{*}{CH}-C_nH_{2n+1} \quad (II)$$
$$\phantom{-}\overset{R_3}{|}$$

$$-\underset{*}{CH}-CH_2-COO-C_nH_{2n+1} \quad (III)$$
$$\phantom{-}\overset{R_3}{|}$$

$$-\underset{*}{CH}-CH_2-CO-C_nH_{2n+1} \quad (IV)$$
$$\phantom{-}\overset{R_3}{|}$$

wherein $R_3$ represents a lower halo-alkyl group having from 1 to 2 carbon atoms; Y represents —COO— when l is 1, and Y represents a single bond when l is o; l represents 0 or 1; n represents an integer of from 1 to 18; and * indicates an optically active center.

2. A liquid crystal compound represented by formula (V):

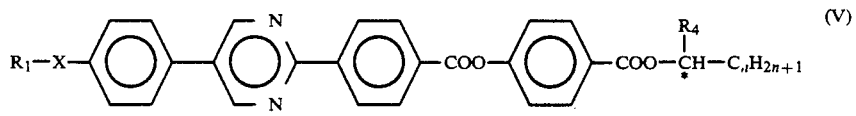

wherein $R_1$ represents an alkyl group having from 1 to 18 carbon atoms; $R_4$ represents $CF_3$ or $C_2F_5$; n represents an integer of from 1 to 18; and * represents an optically active center.

3. A liquid crystal composition which comprises (A) a liquid crystal compound represented by formula (VI) and (B) a liquid crystal compound represented by formula (I):

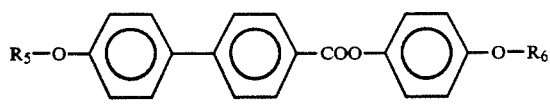
(VI)

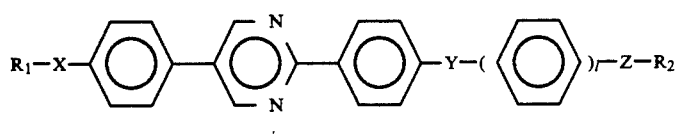
(I)

wherein $R_1$ represents an alkyl group having from 1 to 18 carbon atoms; $R_2$ represents an optically active group represented by formula (II), (III) or (IV):

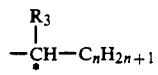
(II)

$$-\underset{*}{C}H-CH_2-COO-C_nH_{2n+1}$$
(III)

$$-\underset{*}{C}H-CH_2-CO-C_nH_{2n+1}$$
(IV)

wherein $R_3$ represents a lower halo-alkyl group having from 1 to 2 carbon atoms; $R_5$ and $R_6$ each represents an alkyl group having from 1 to 18 carbon atoms; Y represents —COO— when l is 1, and Y represents a single bond when l is 0; l represents 0 or 1; n represents an integer of from 1 to 18; and * indicates an optically active center.

* * * * *